(12) United States Patent
Jackson et al.

(10) Patent No.: US 7,024,942 B1
(45) Date of Patent: Apr. 11, 2006

(54) METHOD AND APPARATUS FOR NON-DESTRUCTIVE DETECTION OF PITS AND SEED FRAGMENTS IN FRUIT

(75) Inventors: Eric S. Jackson, Albany, CA (US); Ronald P. Haff, Albany, CA (US); Thomas C. Pearson, Manhattan, KS (US)

(73) Assignee: The United States of America as represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 10/842,792

(22) Filed: May 10, 2004

(51) Int. Cl.
*G01N 3/08* (2006.01)

(52) U.S. Cl. .............................. 73/818; 73/78
(58) Field of Classification Search ................. 73/818, 73/78; 209/485–643; 99/490, 420
See application file for complete search history.

(56) References Cited

U.S. PATENT DOCUMENTS

| | | | |
|---|---|---|---|
| 3,275,136 A | 9/1966 | Allen et al. | |
| 4,009,650 A * | 3/1977 | Lascelles et al. | ............. 99/490 |
| 4,122,951 A * | 10/1978 | Alaminos | .................... 209/545 |
| 4,146,136 A | 3/1979 | Ross et al. | |
| 4,511,046 A | 4/1985 | Walsh et al. | |
| 5,315,879 A | 5/1994 | Crochon et al. | |
| 6,240,766 B1 | 6/2001 | Cawley | |
| 6,553,814 B1 | 4/2003 | de Greef | |

OTHER PUBLICATIONS

Haff, R.P. and Schatzki, T.F., "New Method for Batch Testing of Red Tart Cherries for the Presence of Pits," Journal of Food Processing and Preservation (1994) 18:23-30.

Timm, E.J. et al., "Potential Methods for Detecting Pits in Tart Cherries," Applied Engineering in Agriculture (1991) 7(1):103-109.

* cited by examiner

*Primary Examiner*—Max Noori
(74) *Attorney, Agent, or Firm*—David R. Nicholson; John D. Fado; Leslie Shaw

(57) ABSTRACT

An apparatus and method for the non-destructive detection of pits and pit fragments found in dried fruit has been developed. It utilizes a force transducer and a signal processor to determine whether or not pit or pit fragments are present in a fruit specimen, and is able to automatically separate specimens testing positive from the product stream.

11 Claims, 7 Drawing Sheets

METHOD AND APPARATUS FOR NON-DESTRUCTIVE DETECTION OF PITS AND SEED FRAGMENTS IN FRUIT

BACKGROUND OF THE INVENTION

1. Field of the Invention

The present invention relates to the processing of dried fruit containing pits. Examples of such fruit include, but are not limited to, dried plums (prunes), cherries, peaches, and apricots. Processing in this case refers to non-destructive on-line bulk testing as well as destructive testing for quality control sampling.

2. Background

The presence of pits and pit fragments in harvested fruit such as (but not limited to) dried plums is a matter of concern for processors, causing occasional rejection of product by retail chains as well as injury to consumers which can lead to lawsuits and money damages. In addition to these concerns, the presence of pits has a deleterious effect on the products' quality grade and therefore influences the prices that processors may receive for their product. Some states and/or growers' associations have set minimum acceptable levels for the presence of residual pits and pit fragments in processed fruit. The current allowed level for pits in dried plums processed in California, for example, is 0.025%, or 1 pit fragment for every 400 dried plums. To help achieve this level, fruit processors employ both hand inspection as well as imaging technologies such as machine vision and NIR spectroscopy. While this method helps reduce the number of pits and pit fragments, the problem is a persistent one for the industry. A better method or device is needed to supplement or replace existing technology and would benefit the industry as well as the consumer, with increased quality and product safety.

Efforts put forth by the California Dried Plum Industry are representative of how trade groups and their members are addressing the problem. Currently, this industry employs a combination of devices and proprietary techniques to rid fruit of pits and pit fragments. One popular device in use is the Elliot pitter, for example, which smashes the fruit between two rollers, squeezing the pit out (and sometimes crushing or cracking the pit itself, leaving behind pit fragments).

Another device in use is the Ashlock pitter which employs a conveyor system with mechanical cups holding each piece of fruit in place during the pitting operation. This device uses a pitting head comprised of eight needles, each of which pierces a dried plum and forces the pit out of the fruit and into a pit tube. Up to eight dried plums, therefore, can be pitted with each stroke of the pitting head, assuming each needle successfully engages a single fruit. When the machine is working properly very few pits are missed. However, when the needles are damaged or out of alignment, many pits can be missed or fragmented. The machine requires monitoring and quick maintenance in order to ensure efficient operation, and less than optimal performance can result in a large amount of pits being missed in a short time. Both of these devices, along with other techniques and devices in use, leave behind the occasional pit or pit fragment.

It is also noteworthy that use of the Ashlock pitting device results in the frequent deformation or disfigurement of the fruit being processed. The nature of the deformation depends on a number of factors, including the size of the fruit and its orientation as it passes through the pitter. In general, however, the removal of the pit results in the fruit being partially flattened or forced into a donut-shaped configuration (partially flattened with a hole in the center). Some processors attempt to restore the fruit as close as possible to its original shape. A processing method for fruit which involves temporary deformation, therefore, appears to be acceptable to the industry and is not considered "destructive."

Once the fruit has been through the pitting process, it is necessary to test it for residual pits and pit fragments that may remain. Different methods and devices have been developed for this process and several patents exist on devices for detection of pits in fruit in general. So far, none of these devices adequately addresses the problem. Examples of how others have (inadequately) addressed the problem are set forth below.

One device which has been patented is based on transmission of visible light (U.S. Pat. No. 3,275,136 to Allen et. al., 1964) for detecting seeds in fruit, including cherries. This device suffers from frequent false positives which can be caused by blemished or unusually dense fruit.

U.S. Pat. No. 4,666,045 to Gillepsie and Ricks (1987) discloses a device based on transmittance and sensing of laser light for use with comestibles such as cherries, peaches and other types of fruit containing pits, but was never adopted by the industry due to a lack of accuracy (Timm et al., 1991).

Walsh et al. (1985) patented a device that impales the product with multiple pin-like projections that sense pressure differentials between the needles and the conveyor belt indicating the presence of a defect or irregularity. It seems likely that impaling each piece of fruit with multiple pin-like projections spinning on a wheel would cause damage to the fruit and be considered destructive. At the very least, such handling of the product is likely to lead to loss of quality and susceptibility to post-harvest disease.

Another device, described in U.S. Pat. No. 4,146,136 to Ross et al. (1979), forces the fruit between two rotating wheels to sense the difference in thickness between product with pits and that without. The device utilizes interlocking sets of wheels or rollers with non-adjustable square teeth which operate to impose a limitation on the size of the fruit being tested. The square teeth also appear to damage much of the fruit in the testing process. This device is not able to detect smaller or fragmentary pits, or pits of irregular size or shape (such as those which are irregularly flattened). Such a system also gives rise to many "false positives," resulting in substantial amounts of acceptable product being unjustifiably rejected. The shortcomings of the machine appear to relate to it reliance on simply sensing the crude movement of the deflection of the rollers or wheels as a piece of fruit passes there between, and not on the actual measurement of the forces impinging on said rollers which provides for a much finer detection and control mechanism.

There are a number of patented devices that make use of physical sensors, including force transducers and accelerometers, to evaluate fruit quality, especially for ripeness and firmness. See U.S. Pat. No. 6,240,766 to Cawley (2001); U.S. Pat. No. 5,315,879 to Crochon (1994); U.S. Pat. No. 6,553,814 to deGreef (2003). All of these devices, however, are designed to evaluate the surface quality or density of the fruit and are not intended for detection of pits or pit fragments that lie deep within the fruit. The device described in the deGreef patent, for example, uses a series of wheels which "impact" or bounce off the surface of a rolling piece of fruit, measuring how hard or ripe the fruit is without regard to whether or not a pit or pit fragment lies at the core of the fruit being tested.

Considerable work has also been presented in the scientific literature for detection of pits in cherries. Moreover, the devices used to pit most cherries appear to utilize the same punch and die principle that the Ashlock pitter mentioned above, with the same problem of missed or fragmented pits making their way into the final product. It is plausible that a method that can detect pits in cherries may be applicable to other fruits, although there might be sufficiently significant differences between cherries and other fruits to render any solution to the cherry pit problem inapplicable to other fruits. Still, it is at least of academic interest to note how others have attempted to solve the problem of separating cherries from their pits.

NIR spectroscopy has been attempted to detect cherry pits (Law, 1973) but the results were fairly inconsistent and heavily dependant on fruit size and orientation. Attempts with x-ray have been marginal at best due to the small difference in x-ray absorption between the flesh and the pit at energies high enough to penetrate the product (Brown, as quoted by Timm et al. (1991)). A mechanical device that tests red tart cherries for pits has been reported (Haff and Schatzki, 1994, and Toyofuku and Schatzki, 1999), but this method involves pulping the product (and is therefore destructive) and would not likely be practical for most other fruits such as dried plums (prunes) for example. Finally, Nuclear Magnetic Resonance (NMR) has been used to identify pits in brined cherries (Zion et al., 1995). This method was found to be 97% accurate in classifying both pitted and unpitted cherries, but orientation was critical. Furthermore, NMR equipment is cost prohibitive and unlikely to be adopted by the industry.

Recent visits to several fruit processing plants, as well as communication with the Dried Fruit Association of California (DFA), indicates that none of the aforementioned devices have been adopted as an industry standard and that a reliable pit detection method is still required. In short, the problem of detecting pits and pit fragments in fruit has been surprisingly vexing. What is needed is a reliable and economical device and method that can be used to non-destructively detect pits in various fruits and to remove such affected fruit specimens from the product stream in real-time at a speed that is appropriate for use on-line.

SUMMARY OF THE INVENTION

The apparatus and method disclosed below makes use of a force transducer to detect pits and pit fragments in fruit. It can be used with various types of dried fruit such as, but not limited to, dried plums (prunes), peaches, and apricots.

A non-destructive device was designed and built that can detect and remove dried plums that contain pits from the processing line in real-time.

A major advantage of the invention is its low cost and ease of implementation, especially in comparison to alternative technologies.

Another advantage is that the invention can be used in addition to, and not necessarily as a substitute for, existing testing devices which may already be in place in processing plants, the effect of which will be to boost the efficiency of a processing plant's existing pit detection system.

Still another advantage of the invention is its low "false positive" hit rate, a problem that plagues many other pit detection devices.

Yet another advantage of the invention compared to other devices in this field is its adjustability which permits it to be used to detect small and fragmentary pits for quality control sampling.

Other advantages and attributes of the invention shall become apparent in the disclosure below.

DEFINITIONS

"Stone fruit" refer to any pit-containing fruit such as, but not limited to, prunes (dried plums), cherries, peaches, and apricots.

"Force transducer" refers to a device that produces a voltage output that is proportional to the amount of force applied to a surface.

"Fourier transform" refers to a transformation of an analog signal or waveform into a unique set of numbers representing the frequency information contained in the original signal. "FFT (Fast Fourier Transform)" refers to a computer algorithm commonly used to approximate the Fourier transform of a digital signal.

"Frequency spectra" refers to the magnitudes of the various components of the Fourier (or FFT) transform of a given signal.

"False negatives" refers to the amount of fruit containing pits or pit fragments that are incorrectly classified by the invention as being free of pits or pit fragments.

"False positives" refers to the amount of fruit containing no pits or pit fragments incorrectly classified by the invention as containing pits or pit fragments. False positives are of particular importance because they represent the percentage of the entire product stream that will be diverted, either as waste or to be processed further.

"Singulate" means the process by which fruit specimens are lined-up single file on a conveyor belt so as to permit testing one specimen at a time.

"Modulated force" means controlled, measurable, adjustable, repeatable force, particularly as used in a testing environment.

DETAILED DECSRIPTION OF THE INVENTION

Figure 1:
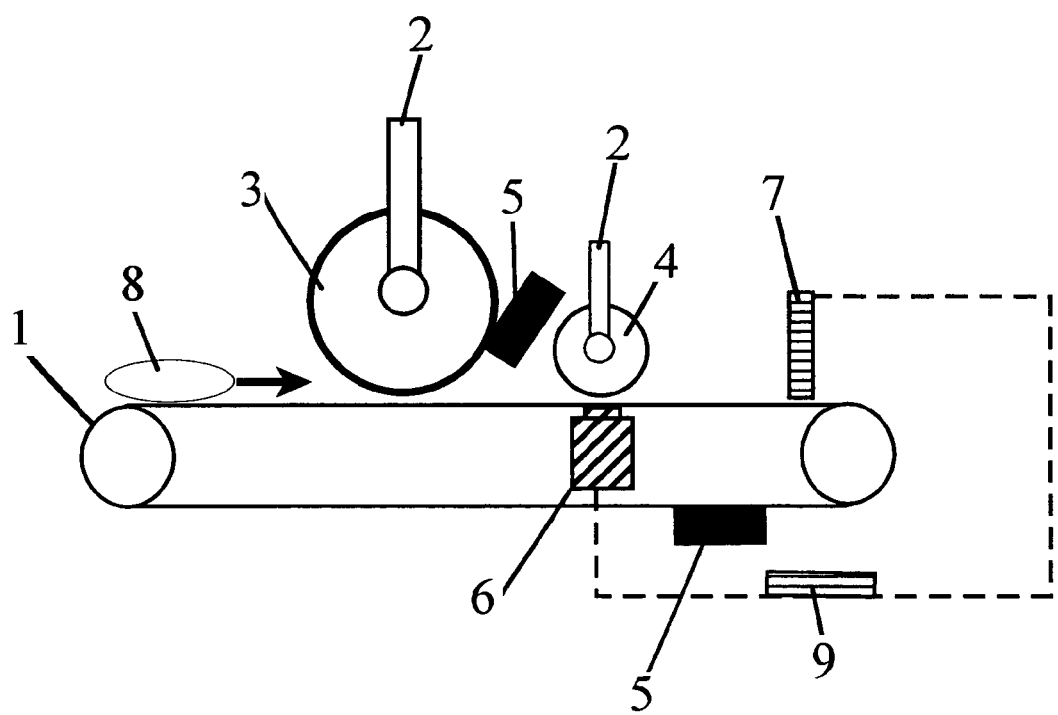
FIG. 1 shows a schematic for the major components of the invention. These components are identified as: a conveyor or continuous belt (1), adjustable shock absorbers (2), a first roller (3), a second roller (4), cleaning device or sponge (5), force transducer (6), rejection mechanism (7), product to be tested (8), and signal conditioning/decision making apparatus (9).
Figure 2:
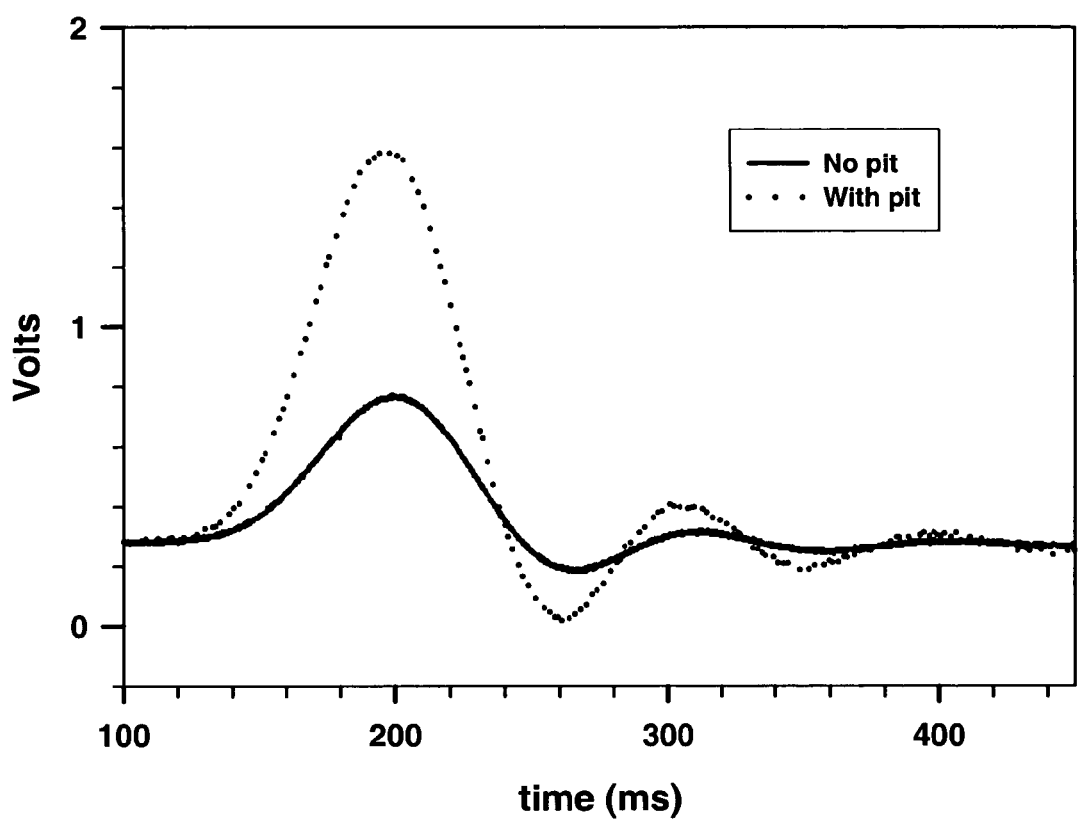
FIG. 2 shows force transducer output for typical pitted and unpitted fruit.

Overall operation of the invention is described in the schematic shown in FIG. 1. Fruit with seeds or pits (8), such as but not limited to dried plums, are introduced single file onto a conveyor or continuous belt (1). The method of singulating, or arranging the individual fruit specimens in single file, on the conveyor belt is dependant on the layout of the processing plant and would have to be designed and built for each particular setup. Devices to accomplish this task are already in use at various points in product processing lines. The singulated fruit is passed between an initial or first roller (3) and the surface of the conveyor belt (1), in effect partially flattening or compressing the fruit before it passes onto the second roller (4). A force transducer (6) is mounted below the conveyor belt (1) and under the second roller (4), said transducer measuring the force on the belt as the fruit (8) passes under the second roller (4). The rollers are optionally mounted on adjustable shock absorbers (2), which allow the product (8) to pass between the roller and the conveyor belt without fragmenting any pits that may be present. Typical voltage outputs from the transducer are shown in FIG. 2. The edible portion of the product (8) is relatively pliable and passes through the gap with minimal force applied to the transducer (6), while pits are unyielding and are pushed downward onto the sensor with much greater force. Therefore, when a fruit containing a pit or pit fragment passes between the second roller (4) and the force transducer (6), a larger output signal results (FIG. 2) which is detected and processed by the signal processor/decision maker (9). When a pit or pit fragment is detected by the signal processor/decision maker (9), a signal is sent to the rejection mechanism or diverter (7) which then rejects the affected fruit specimen from the processing stream. A detailed discussion of each component follows.

Conveyor System

The conveyor system consists of a continuous belt made of food grade Teflon or another material suitable for food processing. The actual dimensions are not critical and may vary, but a typical belt is approximately 10 cm wide and 2 mm thick. It is mounted on two pulleys, approximately but not necessarily 5 cm in diameter, which are affixed on either end of a suitable frame structure such as an aluminum bed. The length of the bed is not critical and may vary, but a frame structure or bed of approximately 90–100 cm in length is generally long enough to include all necessary components and fittings. Typically, an electric, variable speed motor powers the pulleys. As an example, a belt speed set at approximately 50 cm/s will correspond to a potential product throughput of roughly 230 kg/hr for large dried plums (110–130 fruit/kg).

Rollers

The preferred embodiment utilizes two rollers. The "first roller" (3) is the roller which the fruit on the conveyor first encounters and is partially flattened by; the "second roller" (4) is the roller which the flattened fruit next encounters, and where the actual testing or measurement takes place. Both rollers are displaceable and adjustably mounted above the conveyor belt in order to permit the formation of a gap between the bottom of each roller and the top of said conveyor. In other words, between the bottom of the roller and the conveyor belt itself there is a gap that the fruit passes through. These rollers are displaceable and adjustable in order to permit the size of this gap to be modified (increasing or decreasing in width) in order to accommodate different sizes of fruit.

The actual dimensions and composition of the first roller are not critical and may vary but may typically consists of a wood pulley, approximately 15 cm in diameter, 11 cm wide, weighing approximately 6 kg, and overlaid with a coating suitable for food processing such as buna-n rubber that is typically (but not necessarily) 6 mm thick. The rubber coating adds friction to the pulley enabling the fruit to be forced through the gap between the roller and the belt. The relatively large weight of the pulley allows for compression of the fruit pulp or "meat" but is not so heavy as to fragment the pits. A belt driven off the conveyor pulleys (not shown in FIG. 1, but implied) spins the roller in the opposite direction of the conveyor belt to aid in forcing the fruit through the gap. The pulley itself is set on self-compensating shocks to give way for pits and larger pit fragments. These shocks can be adjustable to allow for testing of fruits of different sizes and/or for detection of pits and pit fragments of different sizes. In other words, the sensitivity of the detection device can be in part controlled through the adjustment of the shocks. An example of such a shock is the 12 lb MC25 available from Ace Controls in Farmington, Mich.

The second roller is generally but not necessarily smaller than the first. Typically, it may be made from a pulley approximately but not critically 5 cm in diameter and approximately but not critically 15 cm in width, driven by a low power (e.g. 1/10 horsepower) electric motor. Also, this wheel or roller may be power driven (like the first roller), rotating in a direction opposite to the direction of rotation of the pulleys which drive the conveyor belt. This wheel or roller is coated with friction-inducing material, such as an initial layer of pure gum rubber tubing (ID/OD, 5 cm/7.6 cm) overlaid with a second layer of heat shrink tubing. The heat shrink layer provides resistance to moisture and is easy to clean, yet still provides enough friction to force the fruit through the gap. The roller is also mounted on shock absorbers (e.g. 176 kg MC75-3, Ace Controls, Farmington, Mich.) to provide some shock absorption for pits while forcing them into the transducer to generate a signal. As above, these shocks can be adjustable.

The size of the gap between the rollers and the belt is selected based on the size of the fruit being processed and the desired detection sensitivity. While detection sensitivity increases with increased flattening of the fruit, it is necessary to maintain the gap at a distance that is non-destructive to the product. Specific settings will be discussed below with the experimental procedure. When used for quality control sampling, which is destructive in nature, more rollers can be added with the gaps between the rollers and force transducers gradually becoming smaller, allowing for detection of very small fragments.

Proper operation of the device is heavily dependant on keeping the rollers free of residue from the fruit. Certain fruits present more of a problem than others. Dried plums, for example, have an affinity for sticking to most surfaces. A cleaning device such as a sponge (5), therefore, can be mounted on the first roller and the conveyor belt. The sponges keep the surfaces clean and also knock off any fruit that stick to the surface. The sponges must be kept wet and periodically removed and cleaned.

Force Transducer, Electronics, and Rejection Mechanism

Figure 3:
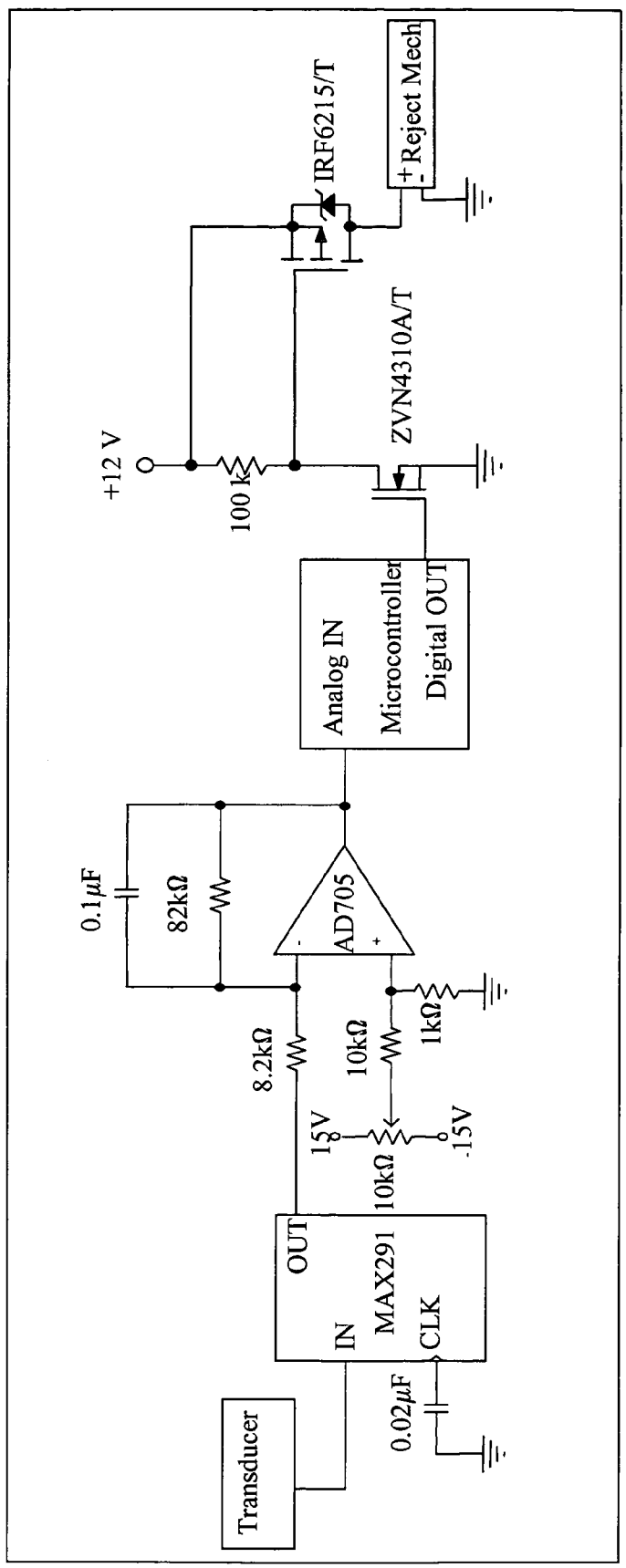
FIG. 3 shows the system electronics, including signal conditioning for amplification and noise filtration of the transducer signal, a programmable microcontroller to run the algorithm, and a switching circuit to drive the reject mechanism.

FIG. 3 shows a circuit diagram and the electronics used to generate the signal from the transducer (6), transmit that signal to a signal processor (9), to make the decision regarding the presence or absence of a pit, and to pass the decision on to the rejection mechanism (7).

A force transducer (6) is mounted underneath the conveyor belt, in line with the second roller (4). An example of a suitable transducer is model 1051V LIVM available from Dytran Instruments, Chatsworth, Calif., which is rated at 50 lb. and capable of producing an analog signal between 0 and 5V. The transducer includes an integral IC unity gain amplifier and a 2 mA power unit. An impact plate that spans the width of the conveyor belt is attached to the top of the transducer (not shown but implied).

Fruit containing a pit causes a larger signal to be generated by the transducer (4) compared to fruit containing no pit. FIG. 2. In either case, the signal is conditioned and sent to the signal processor (9) which incorporates a decision algorithm.

Signal conditioning for the transducer signal is composed of a switched-capacitor filter in order to filter power line and high frequency noise. An example of such a filter is the 8th order, low-pass, Butterworth, switched-capacitor filter (291, Maxim, Sunnyvale, Calif.), with a break frequency of 16.7 Hz. A first-order low-pass filter with a break frequency of 19.4 Hz attenuates clock noise from the switched capacitor filter, adds an additional gain of 10, and provides offset adjustment for the output.

The output from the signal conditioning is measured and passed to a switching circuit to drive the sorting mechanism, which consists of an air nozzle or a mechanical diverter valve (driven by a solenoid) that pushes the undesirable product off of the belt. A microcontroller samples the transducer voltage output at a very high rate (MHz) and captures waveforms representing the force vs. time between the product and the transducer. An analog to digital converter on the microcontroller converts the waveforms into a digital signal for processing. The waveforms are analyzed with the algorithm, and the microcontroller energizes a switching circuit for the reject mechanism if a pit is detected. Two decision algorithms have been developed, each having advantages and disadvantages, and are described below. Depending on the reject mechanism, many switching configurations could be used.

A logic level signal from the microcontroller could drive an n-channel MOSFET (ZVN4310A, Zetex Semiconductors, Hauppauge, N.Y.), which in turn would drive a p-channel power MOSFET (IRF6215, International Rectifier, El Segundo, Calif.). The power MOSFET could supply the appropriate power to a solenoid valve to trigger an air burst or mechanical actuator.

Algorithm 1: The simplest decision algorithm simply measures the maximum voltage output from the transducer for each piece of fruit, and makes a decision based on whether it is above or below a preset value (threshold). This method has the advantage of being simple and inexpensive as the decision can be made with a simple electronic circuit and no computer is required. The disadvantage is slightly less accuracy than algorithm 2, both in terms of false negatives and false positives.

Algorithm 2: An FFT of the signal is performed and two features extracted from the resulting frequency spectra. These features used by the algorithm were selected from a large number of potential features, which were submitted to a discriminate analysis routine. This routine tested all combinations of two and three features for the best separation of pitted from unpitted fruit. The two features which give the best separation, and which are used by the final algorithm, are the maximum spectra magnitude and the magnitude at 33.3 Hz. The advantage of this algorithm over the simpler one described above is in the accuracy of the results, in particular the false positives. The disadvantage is that it requires a computer to be incorporated into the decision making process, increasing the cost and complexity of the apparatus.

EXAMPLES AND EXPERIMENTAL PROCEDURES

The device as described above was assembled and tested at a fruit packing company, using a standard run of large dried plums (sized 52/56 fruit/lb before pitting). A gap of 5 mm was used between the conveyor and rollers. Four hundred dried plums, made up of randomly mixed whole and pitted fruit were placed on the conveyor belt one at a time and the resulting output signals from the force transducer were intercepted and recorded with a digital oscilloscope. Inspection after processing revealed that of the 400 dried plums tested, 186 contained pits and 214 did not. The rejection mechanism was disabled. Each dried plum was examined after processing to determine if a pit was present, and any abnormalities noted. Fruit was removed from the processing line for testing in small batches of ten to twenty, with roughly half taken immediately in front of the pitter and half immediately after. Small batches ensured that the fruit was tested without a significant change in temperature or moisture content from that found on the processing line.

The signals that vary significantly from the averages are generally due to prunes that differ in size from the norm. Whole fruit that are significantly smaller than the norm will contain small pits, resulting in small signals from the transducer and creating false negative results. Improved sorting by size before testing improves the results.

In order for the testing to be non-destructive, the gap between the rollers and the belt must be kept above a minimum distance, dependant on the size of the fruit being tested. Therefore, the device generally is more effective at detecting larger pit fragments which are more likely to cause consumer complaints. For sampling, the fruit does not need to be preserved and the gap can be made narrow enough to detect small pit fragments.

Better results may be obtained by using a series of rollers to flatten out the soft tissue, then passing the remains between the final roller and the transducer with a very small gap. In this manner, pit fragments as small as 1 mm can be detected with very few false positive results.

TRIAL 1

Results for Algorithm 1

Figure 4:
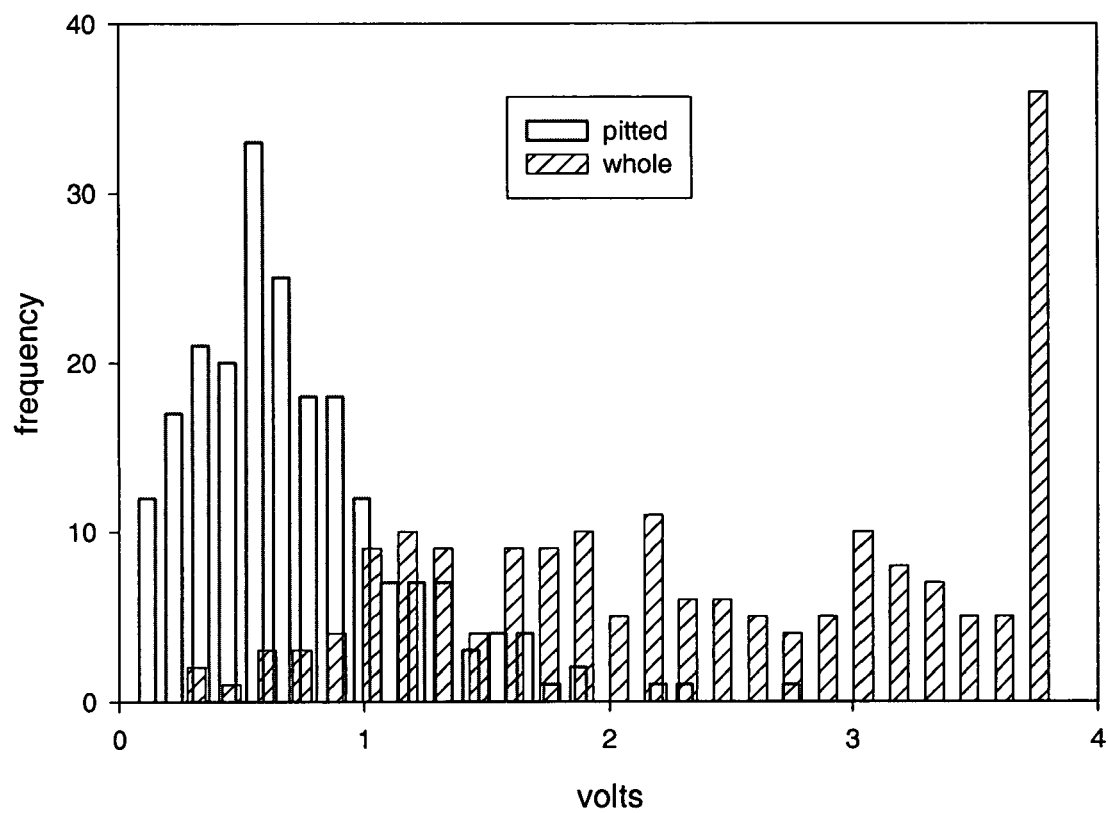
FIG. 4 shows histograms for the pitted and unpitted fruit on the same axis, giving an indication of the amount of overlap in the data.
Figure 5A:
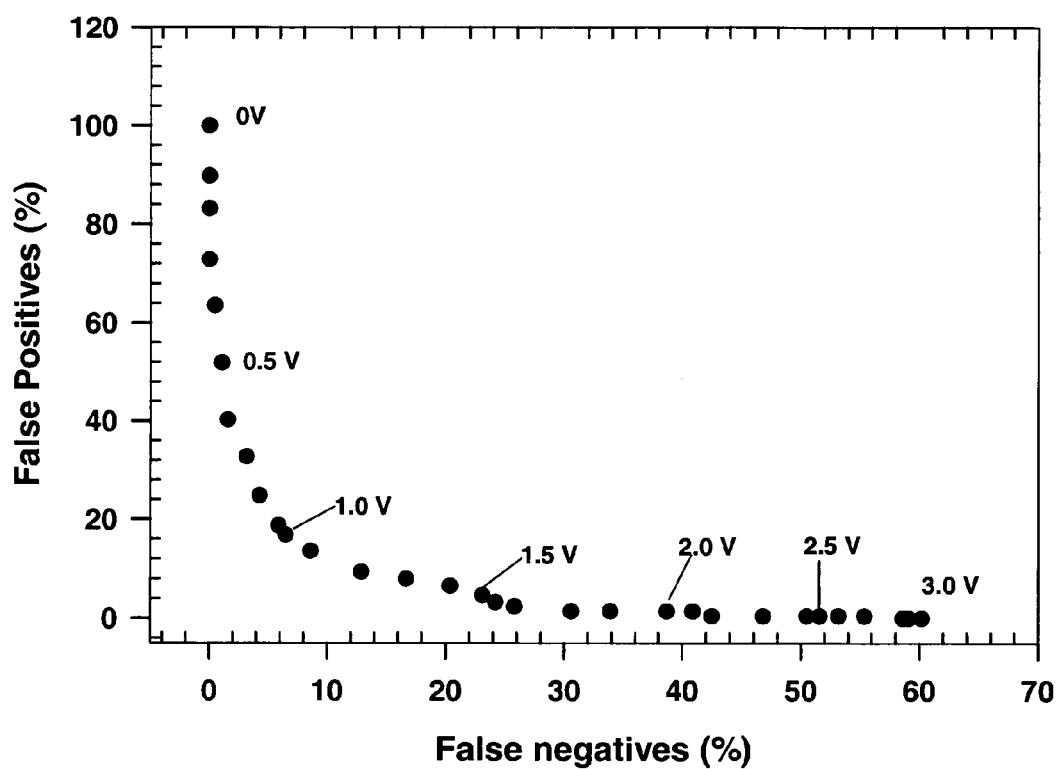
FIG. 5A is a chart showing false negative (fn) compared with false positives (fp) in distinguishing whole from pitted prunes for Trial 1. Each data point represents the percentage of fp vs the percentage of fn (out of 400 prunes tested) given a selected decision threshold, starting at 0 V at the far left and increasing in increments of 0.1 V. The lowest overall error corresponds to a threshold of 1.1 V (see Table 1) but the desired threshold is chosen taking into account the importance of both fp and fn.

Peak amplitude of the output signals ranged from 0 to 2.75 volts for the pitted fruit, and from 0.31 to 3.91 volts for the unpitted. The average peak voltage for the pitted fruit was 0.60 V vs. 2.49 V for the unpitted. FIG. 4 shows histograms for the pitted and unpitted fruit on the same axis, giving an indication of the amount of overlap in the data. FIG. 5(a) shows false negatives vs. false positives for various voltage levels selected as the threshold between a determination of pitted or unpitted. Data for the plot is also presented in table 1 below, which distinguishes between false negatives and false positives based on varying voltage threshold levels:

TABLE 1

| threshold (V) | FN | FP | FN % | FP % | Total Error (%) |
|---|---|---|---|---|---|
| 0.0 | 0 | 214 | 0.0 | 100.0 | 53.5 |
| 0.1 | 0 | 192 | 0.0 | 89.7 | 48.0 |
| 0.2 | 0 | 178 | 0.0 | 83.2 | 44.5 |
| 0.3 | 0 | 156 | 0.0 | 72.9 | 39.0 |
| 0.4 | 1 | 136 | 0.5 | 63.6 | 34.2 |
| 0.5 | 2 | 111 | 1.1 | 51.9 | 28.2 |
| 0.6 | 3 | 86 | 1.6 | 40.2 | 22.2 |
| 0.7 | 6 | 70 | 3.2 | 32.7 | 19.0 |
| 0.8 | 8 | 53 | 4.3 | 24.8 | 15.3 |
| 0.9 | 11 | 40 | 5.9 | 18.7 | 12.8 |
| 1.0 | 12 | 36 | 6.5 | 16.8 | 12.0 |
| 1.1 | 16 | 29 | 8.6 | 13.6 | 11.3 |
| 1.2 | 24 | 20 | 12.9 | 9.3 | 11.0 |
| 1.3 | 31 | 17 | 16.7 | 7.9 | 12.0 |
| 1.4 | 38 | 14 | 20.4 | 6.5 | 13.0 |
| 1.5 | 43 | 10 | 23.1 | 4.7 | 13.3 |
| 1.6 | 45 | 7 | 24.2 | 3.3 | 13.0 |
| 1.7 | 48 | 5 | 25.8 | 2.3 | 13.3 |
| 1.8 | 57 | 3 | 30.6 | 1.4 | 15.0 |
| 1.9 | 63 | 3 | 33.9 | 1.4 | 16.5 |
| 2.0 | 72 | 3 | 38.7 | 1.4 | 18.8 |
| 2.1 | 76 | 3 | 40.9 | 1.4 | 19.8 |
| 2.2 | 79 | 1 | 42.5 | 0.5 | 20.0 |
| 2.3 | 87 | 1 | 46.8 | 0.5 | 22.0 |
| 2.4 | 94 | 1 | 50.5 | 0.5 | 23.8 |
| 2.5 | 96 | 1 | 51.6 | 0.5 | 24.3 |
| 2.6 | 99 | 1 | 53.2 | 0.5 | 25.0 |
| 2.7 | 103 | 1 | 55.4 | 0.5 | 26.0 |
| 2.8 | 109 | 0 | 58.6 | 0.0 | 27.3 |
| 2.9 | 110 | 0 | 59.1 | 0.0 | 27.5 |
| 3.0 | 112 | 0 | 60.2 | 0.0 | 28.0 |

The minimum error was 11.0% (89% correctly classified) with a threshold setting of 1.2 V. The corresponding false positive rate was 9.3%. With a threshold setting of 1.8 V false positives fall to 1.4% while still detecting around 70% of the product with pits remaining.

Trial 1—Results for Algorithm 2

Figure 6:
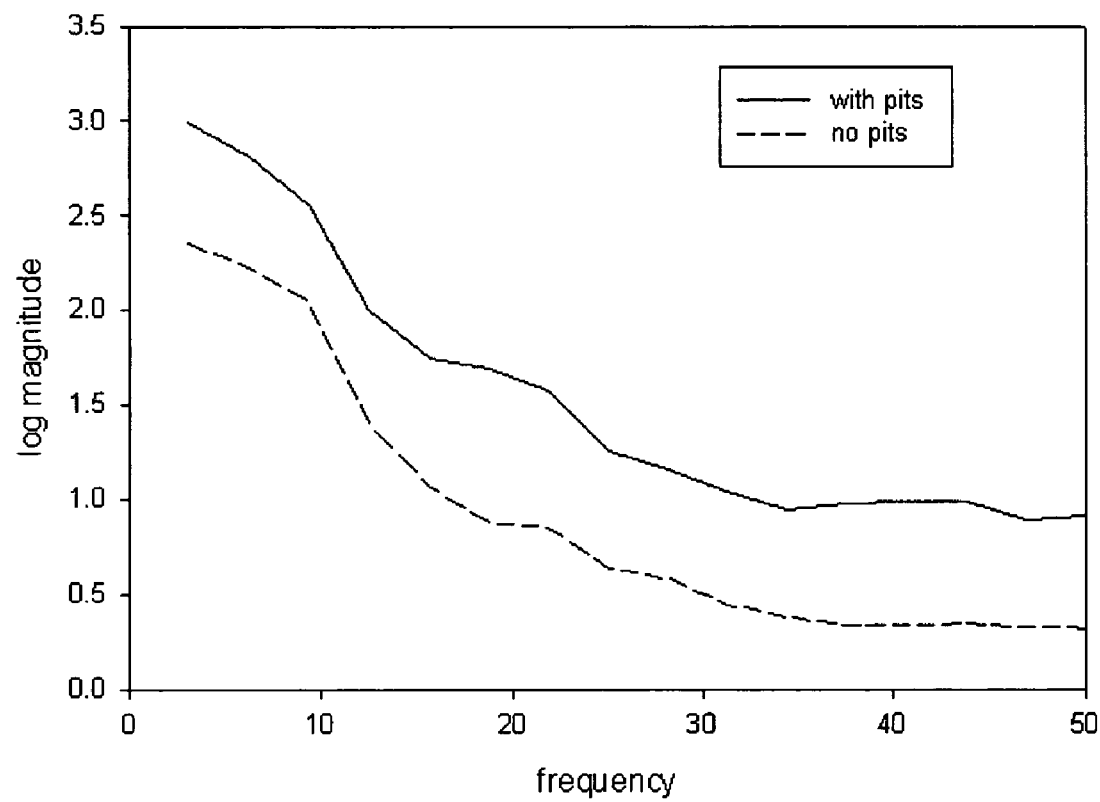
FIG. 6 shows the average frequency spectra of prune force signals for Trial 1.

Frequency spectra magnitudes were found to be most useful for classify pitted prunes from those still with pits. The average spectra are shown in FIG. 6. Note that prunes with pits generally have higher magnitudes across the frequency spectrum and, additionally, the shapes of the curves are slightly different. The frequency spectra of prunes without pits have a weak tendency to have lower magnitudes at higher frequencies relative their maximum magnitude.

The best classification accuracy was obtained with two features: the maximum magnitude of the frequency spectra and the spectra magnitude corresponding to 31.3 Hz. The classification accuracy was 99.1% for pitted prunes and 75.3% for prunes with pits. This corresponds to removal of 75% of prunes with pits with less than 1% false positives.

Trial 2

For Trial 2, the dried plums (prunes) tested were somewhat larger than those in trial one, in the 42/46 fruit/lb category.

Trial 2—Results for Algorithm 1

Figure 5B:
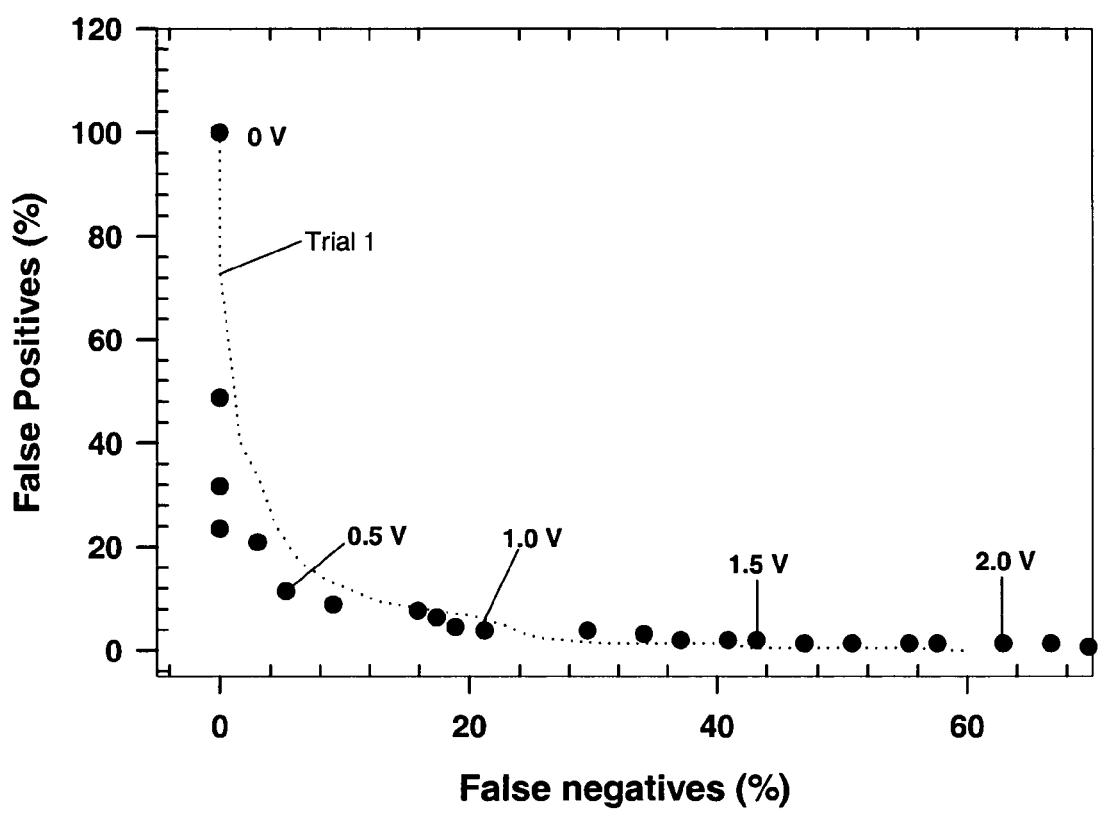
FIG. 5B is a chart showing false negative (fn) compared with false positives (fp) in distinguishing whole from pitted prunes for Trial 2. The lowest overall error corresponds to a threshold of 0.5 V. The data is presented in Table 2.

A gap of 2.5 mm was used between the conveyor and first roller, and the gap at the second roller remained unchanged at 5 mm. Otherwise, testing conditions were the same as for trial 1. Of 290 dried plums tested, 132 contained pits and 158 did not. FIG. 5(b) shows false negatives vs. false positives for various voltage levels selected as the threshold between a determination of pitted or unpitted.

Each data point in FIG. 5(b) represents the results of the test of 290 prunes, and the data can be seen in Table 2:

TABLE 2

| threshold (V) | FN | FP | FN % | FP % | Total Error (%) |
|---|---|---|---|---|---|
| 0.0 | 0 | 158 | 0.0 | 100.0 | 45.8 |
| 0.1 | 0 | 77 | 0.0 | 48.7 | 22.3 |
| 0.2 | 0 | 50 | 0.0 | 31.7 | 14.5 |
| 0.3 | 0 | 37 | 0.0 | 23.4 | 10.7 |
| 0.4 | 4 | 33 | 3.0 | 20.9 | 10.7 |
| 0.5 | 7 | 18 | 5.3 | 11.4 | 7.3 |
| 0.6 | 12 | 14 | 9.1 | 8.9 | 7.5 |
| 0.7 | 21 | 12 | 15.9 | 7.6 | 9.6 |
| 0.8 | 23 | 10 | 17.4 | 6.3 | 9.6 |
| 0.9 | 25 | 7 | 18.9 | 4.4 | 9.3 |
| 1.0 | 28 | 6 | 21.2 | 3.8 | 9.9 |
| 1.1 | 39 | 6 | 29.5 | 3.8 | 13.1 |
| 1.2 | 45 | 5 | 34.1 | 3.2 | 14.5 |
| 1.3 | 49 | 3 | 37.1 | 1.9 | 15.1 |
| 1.4 | 54 | 3 | 40.9 | 1.9 | 16.5 |
| 1.5 | 57 | 3 | 43.2 | 1.9 | 17.4 |
| 1.6 | 62 | 2 | 47.0 | 1.3 | 18.6 |
| 1.7 | 67 | 2 | 50.8 | 1.3 | 20.0 |
| 1.8 | 73 | 2 | 55.3 | 1.3 | 21.8 |
| 1.9 | 76 | 2 | 57.6 | 1.3 | 22.6 |
| 2.0 | 83 | 2 | 62.9 | 1.3 | 24.7 |
| 2.1 | 88 | 2 | 66.7 | 1.3 | 26.1 |
| 2.2 | 92 | 1 | 69.7 | 0.6 | 27.0 |
| 2.3 | 95 | 1 | 72.0 | 0.6 | 27.8 |
| 2.4 | 99 | 1 | 75.0 | 0.6 | 29.0 |
| 2.5 | 102 | 1 | 77.3 | 0.6 | 29.9 |
| 2.6 | 108 | 1 | 81.8 | 0.6 | 31.6 |
| 2.7 | 111 | 1 | 84.1 | 0.6 | 32.5 |
| 2.8 | 112 | 0 | 84.8 | 0.0 | 32.5 |
| 2.9 | 113 | 0 | 85.6 | 0.0 | 32.8 |
| 3.0 | 116 | 0 | 87.9 | 0.0 | 33.6 |

The minimum error was 7.3% (92.7% correctly classified) with a threshold setting of 0.5 V. The corresponding false positive rate was 11.4%.

Peak amplitude of the output signals ranged from 0 to 2.72 volts for the pitted fruit, and from 0.31 to 3.58 volts for the unpitted, virtually unchanged from the first trial. The average peak voltage for the pitted fruit was 0.23 V vs. 1.77 V for the unpitted.

Trial 2—Results for Algorithm 2

The classification accuracy using the second algorithm for the larger prunes of trial 2 was 98.7% for pitted prunes and 67.4% for prunes with pits.

CONCLUSION

The results indicate that using this invention in conjunction with existing technology has the potential to reduce the pit count in the final product by roughly 70–75%, depending on the algorithm used and the size of the prunes being processed, while rejecting approximately 1% as false positives. The low false positive rate, coupled with the low cost of the invention, suggest that this invention would be attractive to the industry. Over 90% of pits can be detected if a higher false positive rate is acceptable. With existing technology, rejected product is often hand sorted or retested.

One of the benefits of this technology over others in use in processing plants is the cost of the device. Materials to build the device cost less than $500 in total, the bulk of which covered the cost of motors and the force transducer. This is much more economical than NIR and machine vision technology, which generally cost tens of thousands of dollars and are still only marginally effective.

What is claimed is:

1. An apparatus for non-destructive detection of pits and seed fragments in dried fruit comprising:
   a. A conveyor belt
   b. A first roller for partially flattening a fruit specimen;
   c. A second roller for applying modulated force on said partially flattened fruit specimen;
   d. Means to measure the amount of said modulated force which is transmitted by said second roller through said fruit specimen; and
   e. Means to reject a fruit specimen which transmits a level of force at or above a threshold level.

2. The apparatus of claim 1 wherein the means to measure said modulated force is a force transducer.

3. The apparatus of claim 2 further comprising an apparatus for signal conditioning and decision making.

4. The apparatus of claim 3, further comprising at least one shock absorber attached to at least one of said rollers.

5. The apparatus of claim 4 wherein said shock absorber is adjustable thereby permitting the regulation of the amount of force to be transmitted to said fruit specimens.

6. The apparatus of claim 5, further comprising cleaning means for cleaning said conveyor belt of fruit specimens and fragments of fruit specimens.

7. An apparatus for detecting dried fruit containing pits or pit fragments, comprising
   a. a continuous belt;
   b. power-actuated roller means for setting said belt in motion;
   c. compressing means for compressing dried fruit to be tested for the presence of pits or pit fragments;
   d. detection means for determining whether said compressed dried fruit contains a pit or pit fragment; and
   e. rejection means for rejecting dried fruit containing a pit or pit fragment.

8. The apparatus of claim 7 wherein said compressing means is a shock absorber-equipped first roller adjustably mounted above said continuous belt.

9. The apparatus of claim 8 wherein said detection means is a second roller adjustably mounted above said continuous belt and a force transducer mounted below said continuous belt.

10. The apparatus of claim 9 wherein said detection means is further comprised of a signal conditioner.

11. The apparatus of claim 10 further comprising a means to clean said continuous belt of dried fruit and dried fruit fragments.

* * * * *